United States Patent [19]

Takahashi

[11] 4,423,932
[45] Jan. 3, 1984

[54] EYE FUNDUS OBSERVING AND PHOTOGRAPHING OPTICAL SYSTEM

[75] Inventor: Fumio Takahashi, Yokohama, Japan

[73] Assignee: Nippon Kogaku K.K., Tokyo, Japan

[21] Appl. No.: 214,043

[22] Filed: Dec. 8, 1980

[30] Foreign Application Priority Data

Dec. 25, 1979 [JP] Japan ................................ 54-167645

[51] Int. Cl.³ .......................... A61B 3/14; G03B 29/00
[52] U.S. Cl. ..................................... 351/207; 351/221
[58] Field of Search ..................... 351/6, 7, 13, 14, 16, 351/207, 206, 211, 221

[56] References Cited

U.S. PATENT DOCUMENTS 4,162,827  7/1979  Ito ........................................... 351/7
4,176,920  12/1979  Ito ........................................... 351/7
4,322,137  3/1982  Nohda ..................................... 351/7

*Primary Examiner*—R. A. Rosenberger
*Attorney, Agent, or Firm*—Fitzpatrick, Cella, Harper & Scinto

[57] ABSTRACT

An eye fundus observing and photographing optical system has an objective lens including a main positive lens component and at least one positive lens component provided at that side of the main positive lens component which is adjacent to an eye to be examined, and an illuminating optical system including an apertured mirror disposed obliquely with respect to the optical axis of the objective lens to supply an illuminating light to the fundus of the eye through the objective lens. The reflected image position of the opening portion of the apertured mirror by the lens surface of said at least one positive lens component which is adjacent to the eye is made substantially coincident with a first position whereat the reflected image of the opening portion of the apertured mirror by the lens surface of the main positive lens component which is adjacent to the eye is formed, and the reflected image position of the opening portion of the apertured mirror by the lens surface of said at least one positive lens component which is adjacent to the apertured mirror is made substantially coincident with a second position which is more adjacent to the eye than said first position.

2 Claims, 7 Drawing Figures

PRIOR ART FIG. 1
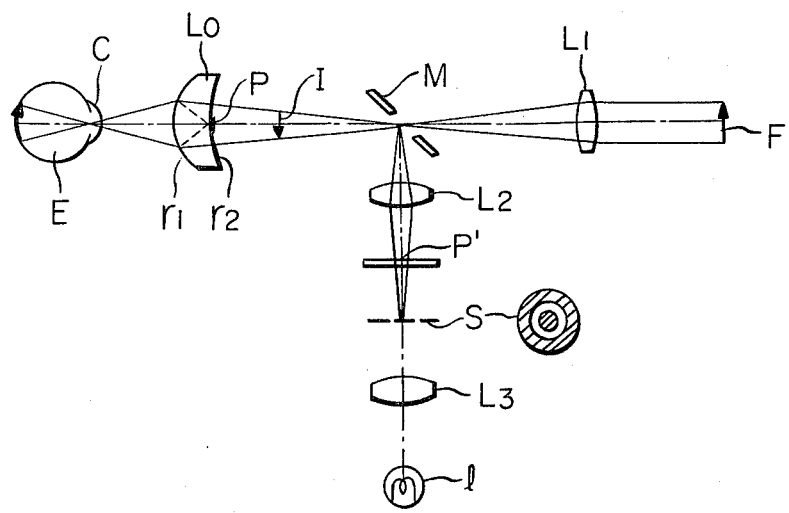
FIG. 2
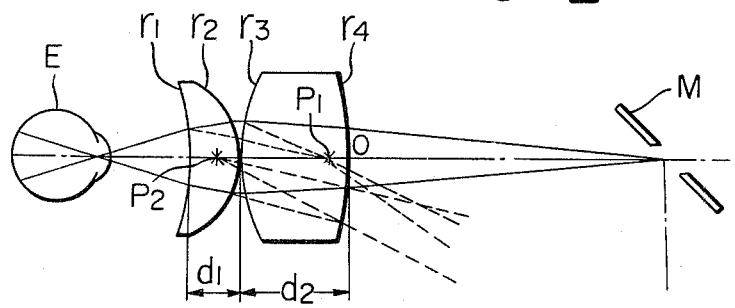
FIG. 3
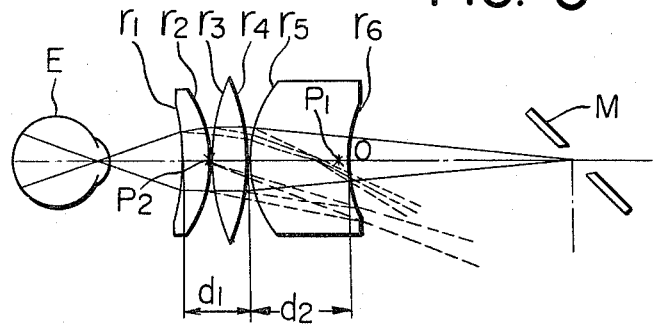

EYE FUNDUS OBSERVING AND PHOTOGRAPHING OPTICAL SYSTEM

BACKGROUND OF THE INVENTION

1. Field of the Invention

This invention relates to a device for observing and photographing the fundus of an eye, and particularly to the optical system thereof.

2. Description of the Prior Art

In an eye fundus observing and photographing optical system of the type in which an objective lens is used in common for an illuminating optical system and an observing/photographing optical system, if the reflected light by the surface of the objective lens of the illuminating optical system mixes with the observation/photographing light beam, the quality of the image of the eye fundus will be greatly deteriorated. For this reason, various contrivances have heretofore been made, but the curvatures of the lens surfaces and the number of lenses have been limited for the elimination of the reflected light and it has been very difficult to design an objective lens which enables observation and photographing over a wide angle of view.

FIG. 1 of the accompanying drawings shows an example of the eye fundus photographing optical system using a meniscus type objective lens heretofore widely used. In FIG. 1, E designates an eye to be examined, C a cornea, $L_0$ a meniscus type objective lens, M an apertured mirror, $L_1$ a relay lens of the photographing system, and F a film surface. An illuminating lamp l illuminates a ring slit S through a condenser lens $L_3$. This ring slit S is once imaged near the position of the apertured mirror M disposed obliquely with respect to the optical axis by a relay lens $L_2$ of the illuminating system, and is further imaged on the corner C of the eye E by the objective lens $L_0$ through the apertured mirror M, thus illuminating the fundus of the eye. The light beam leaving the fundus of the eye E passes through the center of the pupil of the eye and once forms an inverted eye fundus intermediate image I by the objective lens $L_0$, and then passes through the opening portion of the apertured mirror M and forms an erect eye fundus image on the film surface F by the relay lens $L_1$ of the photographing system.

As is well-known, to prevent mixing of a reflected light created by the cornea C of the eye E, the illuminating light beam is separated from the photographing light beam passing through the center of the pupil of the eye E by a so-called ring illumination using the ring slit S.

In this meniscus type objective lens $L_0$, the center of curvature of the second surface $r_2$ thereof is the position at which the apertured mirror intersects the optical axis and therefore, the light beam emitted from the central position returns along the same light path when reflected by the surface $r_2$. That is, the position at which the apertured mirror M intersects the optical axis is in equal magnification and real conjugate relation with respect to the reflecting surface which is the second surface $r_2$ of the objective lens $L_0$ and therefore, if the illuminating light beam and the photographing light beam are separate from each other like the well-known ring illumination, the reflected light of the illuminating system by the second surface $r_2$ will never mix with the photographing light beam. In the first surface $r_1$ of the objective lens $L_0$ which is the surface adjacent to the eye to be examined, the curvature of the first surface $r_1$ is determined so that the reflected light of the illuminating system by this surface gathers near the vertex of the second surface $r_2$, and a black point P of sufficient size to intercept the reflected light passing through the opening portion of the apertured mirror M may be disposed near the vertex of the second surface $r_2$, thereby eliminating the reflected light in this surface. Instead of placing the real black point P near the vertex of the second surface $r_2$ of the objective lens, even by obtaining a conjugate position thereof in the illuminating system as shown in FIG. 1 and placing a black point P' at that position, it is of course possible to eliminate the reflected light.

However, in such meniscus type objective lens, the angle of view of about 30° has been the limit and a wider angle of view could not be expected.

In order to provide a wider angle of view for an objective lens, a greater number of lenses, namely, refracting surfaces, becomes necessary to bear the refractive power, but as in the above-described example, elimination of the reflected light in each lens surface, of the illuminating light, is indispensable. Therefore, if a black point is provided at the reflected image position in each lens surface, a number of black points corresponding to the number of surfaces will exist and intercept the reflected light itself from the fundus of the eye to be examined which is originally necessary. In recent years, various propositions have been made as to how to eliminate efficiently the reflected light in the lens surface, but there has been obtained no sufficient device.

SUMMARY OF THE INVENTION

It is the object of the present invention to provide an eye fundus observing and photographing optical system in which the reflected light in the lens surface is sufficiently eliminated and which enables observation or photographing of the fundus of an eye in a wider range of angle of view.

The eye fundus observing and photographing optical system according to the present invention has an objective lens including a main positive lens component and at least one positive lens component provided at that side of said main positive lens component which is adjacent to an eye to be examined, and an illuminating optical system including an apertured mirror disposed obliquely with respect to the optical axis of said objective lens to supply an illuminating light to the fundus of said eye through said objective lens. The reflected image position of the opening portion of said apertured mirror by the lens surface of said at least one positive lens component which is adjacent to said eye is made substantially coincident with a first position $P_1$ whereat the reflected image of the opening portion of said apertured mirror by the lens surface of said main positive lens component which is adjacent to said eye is formed, and the reflected image position of the opening portion of said apertured mirror by the lens surface of said at least one positive lens component which is adjacent to said apertured mirror is made substantially coincident with a second position $P_2$ which is more adjacent to said eye than said first position.

The invention will become more fully apparent from the following detailed description thereof taken in conjunction with the accompanying drawings.

BRIEF DESCRIPTION OF THE DRAWINGS

FIG. 1 shows an example of the eye fundus photographing optical system according to the prior art.

FIGS. 2 and 3 are lens construction views of a first and a second embodiment of the objective lens according to the present invention.

DESCRIPTION OF THE PREFERRED EMBODIMENTS

Figure 4:
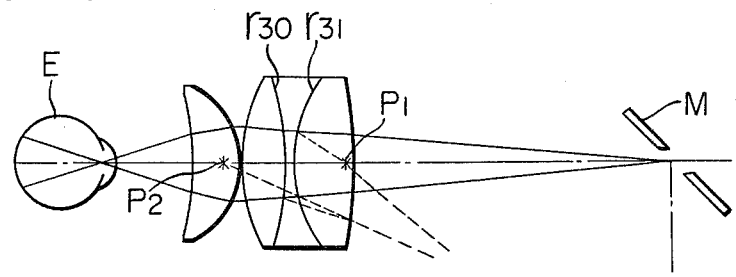
FIG. 4 shows an objective lens having a cemented surface for the correction of chromatic aberration in the first embodiment.

Embodiments of the present invention will hereinafter be described. FIGS. 2 and 3 are lens construction views of a first and a second embodiment of the objective lens according to the present invention, and for simplicity of illustration, the cemented surfaces of the lens are not shown therein and of the optical system of the eye fundus camera, only the eye E to be examined and an apertured mirror M are shown therein.

The first embodiment of FIG. 2 uses a biconvex type lens as a main positive lens and combines therewith a positive meniscus lens having its concave surface facing the examined eye side as a lens having a positive refractive power. If the successive lens surfaces are defined as $r_1$, $r_2$, $r_3$ and $r_4$ in succession from the examined eye side, the light reflected by the odd-numbered lens surfaces, namely, the surfaces of the successive lenses which are adjacent to the examined eye side, exits toward the apertured mirror side and forms a reflected image of the opening portion of the apertured mirror, and the curvatures of these surfaces are determined so that the position of the reflected image is coincident with or near a first position which is a point $P_1$ adjacent to the apertured mirror side, and likewise, the curvatures of the even-numbered lens surfaces, namely, the surfaces of the successive lenses which are adjacent to the apertured mirror side, are determined so that the reflected image of the illuminating system formed by such surfaces is coincident with or near a second position which is a point $P_2$ more adjacent to the examined eye side than the point $P_1$.

The second embodiment shown in FIG. 3 uses, as a main positive lens component, a conventional meniscus type lens as shown in FIG. 1 and combines a positive meniscus lens having its concave surface facing the examined eye side and a biconvex lens as two lenses having a positive refractive power on the examined eye side. If the successive lens surfaces are defined as $r_1$, $r_2$, ..., $r_6$ in succession from the examined eye side, the center of curvature of the last surface $r_6$ is positioned at a point whereat the apertured mirror intersects the optical axis and therefore, as in the case of the conventional meniscus type lens, of the illuminating light, the light reflected by this surface $r_6$ does not pass through the opening portion of the apertured mirror to mix with the phototaking light path. The curvatures of the successive surfaces are determined so that, as in the first embodiment, the position of the reflected image by the odd-numbered surfaces of $r_1$ to $r_5$, namely, the lens surfaces which are adjacent to the examined eye side, is coincident with or near the first position which is the point $P_1$ adjacent to the apertured mirror side, of the two points $P_1$ and $P_2$, while the reflected image by the even-numbered surfaces is coincident with or near the second position which is the point $P_2$ adjacent to the examined eye side.

Thus, in the present invention wherein the position of the reflected image by each surface is made coincident with two locations depending on whether the lens surface is adjacent to the examined eye side or the apertured mirror side, the size of a black point or a black point image to be set at the two locations on which the reflected image concentrates is determined by the size of the reflected image, namely, the magnification of the reflected image and therefore, it is necessary to make this magnification as small as possible. Also, from various points of view, it is desirable that the two points $P_1$ and $P_2$ be set under the following conditions. That is, when the distance from the vertex of the lens surface which is most adjacent to the examined eye side to the vertex of the lens surface of the main positive lens component which is adjacent to the examined eye side is $d_1$, the center thickness of the main positive lens component is $d_2$, the vertex of the lens surface of the main positive lens component which is adjacent to the apertured mirror side is the origin 0 of the coordinates and the apertured mirror side is the positive direction, then it is desirable that positions $P_1$ and $P_2$ whereat the reflected image is formed be in the following ranges.

$$-\tfrac{1}{3}d_2 \leq P_1 < d_2 \qquad (I)$$

$$-(2d_1+d_2) \leq P_2 \leq (d_1/4)d_2 \qquad (II)$$

These conditions will hereinafter be explained.

EXPLANATION OF CONDITION (I)

As the first reflected image position $P_1$ is shifted toward the examined eye E side, the curvature radius of the surface of the lens surfaces which is adjacent to the examined eye side, specifically, the surface $r_3$ in the first type of FIG. 2 and the surface $r_5$, particularly, the surface $r_1$, in the second type of FIG. 3, becomes smaller and correspondingly, the curvature radius of the surface $r_2$ also becomes smaller in connection with condition (II), and the refractive powers in these surfaces become excessively great and the operating distance becomes shorter. Accordingly, if the lower limit of said range is exceeded, the curvature radius of the surface $r_1$ also becomes smaller in both the type of FIGS. 2 and 3 and this, coupled with the fact that the operating distance is extremely short, comes to cover the eyeball and becomes actually unusable. Conversely, as the first reflected image position $P_1$ is shifted toward the apertured mirror M side, the curvature radius of the surface $r_1$, becomes smaller in the first type of FIG. 2 but the reflected image magnification in this surface becomes greater and, in the second type of FIG. 3, the curvature radius of the surface $r_5$ becomes greater and also the curvature radii of the surfaces $r_1$, $r_3$ and $r_4$ become greater and the reflected image magnification becomes greater. Accordingly, if the upper limit of said range is exceeded, a large black point will become necessary and the shadow of the black point will be created in the observation view field and the device will become impractical. Also, where the first position $P_1$ lies on the apertured mirror side, it becomes near the position of the eye fundus image, particularly, the eye fundus image position of emmetropia or hypermetropia and the black point becomes liable to be conspicuous in the eye fundus image and also, the refractive power of each lens surface becomes smaller and cannot correspond to a wide angle of view and therefore, from these points of view, said range is desirable.

EXPLANATION OF CONDITION (II)

As the second reflected image position $P_2$ is shifted toward the examined eye E side, the curvature radii of the surfaces of the lenses which are adjacent to the apertured mirror side (in the first type of FIG. 2, the surface $r_2$ and particularly the surface $r_4$, and in the second type of FIG. 3, the surfaces $r_2$ and $r_4$) become greater, and the image of the opening portion of the apertured mirror by the light rays reflected by these lens surfaces becomes larger, and the black point required to intercept the reflected light also becomes larger. If said range is exceeded, the reflected image magnification in these lens surfaces exceeds 0.8-0.9, and a large black point comparable to a ring slit image formed at the position of the apertured mirror is required and the shadow of the large black point is created in the center of the view field. Also, in both the types of FIGS. 2 and 3, the refractive power of each lens surface becomes smaller and it becomes difficult to maintain a wide angle of view. Conversely, as the second position $P_2$ is shifted toward the apertured mirror M side, the curvature radii of the surfaces of the lenses which are adjacent to the apertured mirror side (in the first type of FIG. 2, the surface $r_2$, and in the second type of FIG. 3, the surface $r_4$ and particularly the surface $r_2$) become smaller and the refractive powers in these surfaces become excessively great and the operating distance becomes shorter. If said range is exceeded, in both the types of FIGS. 2 and 3, the curvature radius of the surface $r_1$ will become smaller and this, coupled with the fact that the operating distance is extremely short, comes to cover the eyeball and becomes actually unusable.

Also, a conjugate black point or a black point image generally lies near the eye fundus image position of an intense myopia and therefore, during the photographing of emmetropia or weak myopia, the black point image is not conspicuous due to the defocus. However, in the construction of the present invention, if the ranges of said two conditions, particularly, the upper limits thereof, are exceeded, the black point of the black point image lies near the eye fundus image position of emmetropia and further, of hypermetropia, and therefore, the frequency with which a clear black point is photographed becomes higher, thus hampering the observation of the eye fundus image.

Figure 5:
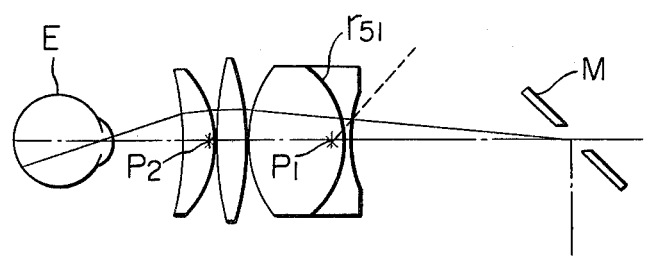
FIG. 5 shows an objective lens having a cemented surface for the correction of chromatic aberration in the second embodiment.

With respect to the lens surface of each lens which is adjacent to the examined eye side and the lens surface of each lens which is adjacent to the apertured mirror side, description has hitherto been made of the desirable conditions regarding the positions $P_1$ and $P_2$ of the reflected image by the respective lens surfaces, but actually, to correct the chromatic aberration well, it becomes necessary to provide a cemented surface in any of the lens components. In order to eliminate even the light rays reflected by this cemented surface, the curvature of the cemented surface may be chosen so that even the position of the reflected image of the opening portion of the apertured mirror by the cemented surface is coincident with said point $P_1$ or $P_2$, and the curvature of the cemented surface is determined with the chromatic aberration or the like taken into account. Specifically, in the first type shown as the first embodiment in FIG. 2, as shown in FIG. 4, the biconvex main positive lens is provided with two cemented surfaces, namely, a cemented surface $r_{30}$ having its convex surface facing the mirror side and a cemented surface $r_{31}$ having its concave surface facing the mirror side, so that the reflected image position by the former $r_{30}$ is coincident with the point $P_2$ and the reflected image position by the latter $r_{31}$ is coincident with the point $P_1$. Also, in the second type shown as the second embodiment in FIG. 3, as shown in FIG. 5, a meniscus-shaped main positive lens component is provided with a cemented surface $r_{51}$ having its convex surface facing the mirror side, so that the reflected image position by this cemented surface is coincident with the point $P_1$. In FIGS. 4 and 5, of the reflected light reflected by each surface, only the light rays reflected by the cemented surfaces are indicated by dotted lines. The conditions of the reflected light on the surface in contact with the air are as shown in FIGS. 2 and 3.

It is desirable that these cemented surfaces for the correction of the chromatic aberration be determined with the reflected image position being further taken into consideration as follows.

In the first type as shown in FIG. 4, when the position $P_1$ is shifted toward the apertured mirror M side and the position $P_2$ is shifted toward the examined eye E side and, in the second type as shown in FIG. 5, when the position $P_1$ is shifted toward the examined eye E side, the curvature radii of the surfaces $r_{30}$, $r_{31}$ and $r_{51}$ become greater, but there is no particular limitation in this direction. In the second type of FIG. 5, it is also possible to determine the curvature radius of the surface $r_{51}$ so that the reflected image position by the surface $r_{51}$ is the position $P_2$, but in this case, the reflected image magnification is great and a difficulty is encountered from the viewpoint of the correction of chromatic aberration.

Conversely, in the first type of FIG. 4, when $P_1$ and $P_2$ are shifted toward the examined eye E side and the apertured mirror M side, respectively, and in the second type of FIG. 5, when $P_1$ is shifted toward the apertured mirror M side, the curvature radii of the surfaces $r_{30}$, $r_{31}$ and $r_{51}$ become smaller. With regard to the surface $r_{30}$, if it is within said range, there will be no particular problem, but with regard to the surface $r_{31}$, the position $P_1$ should more desirably be up to about $-\frac{1}{3}d_2$, namely, $-\frac{1}{3}d_2 \leq P_1 < d_2$. Also, with regard to the surface $r_{51}$ in the second type of FIG. 5, the position $P_1$ should more desirably be up to $-(1/10)d_2$, namely, as narrow as $-\frac{1}{3}d_2 \leq P_1 < -(1/10)d_2$.

Further, where, as in the first type of FIG. 4, a cemented surface $r_{31}$ having its concave surface facing the apertured mirror side exists in the last lens group, if the curvature radius of this surface is made too small, there will be a fear that the illuminating light is twice reflected by this surface and passes through the opening portion of the apertured mirror and from this point of view, it is desirable that $P_1$ be within said range.

If said range is exceeded, the curvature radius will become extremely small and a sufficient effective diameter may not be secured and in reality, it will become difficult to achieve a device of sufficiently good performance.

Figure 7:
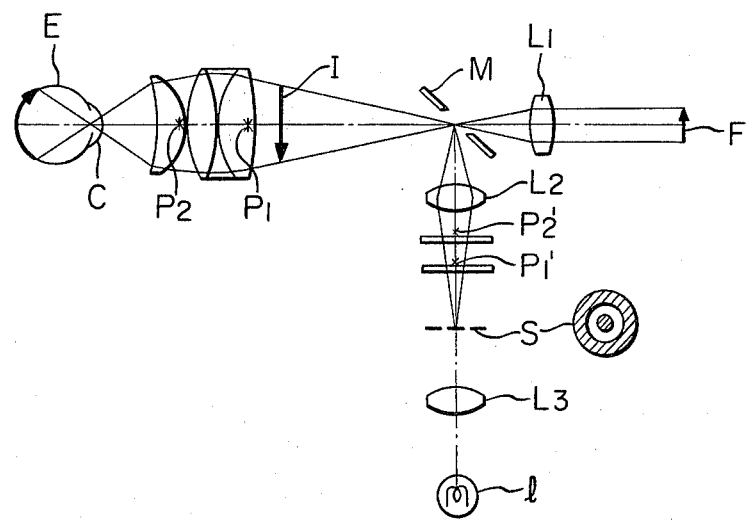
FIG. 7 shows an example of the eye fundus observing and photographing optical system using the objective lens of FIG. 4.

In each of the above-described embodiments, as shown in FIG. 7, the points $P_1$ and $P_2$ of the reflected image position and the position in real conjugate relation with respect to a relay lens $L_2$ are respectively obtained in the illuminating system and a black point of a sufficient size to intercept the reflected light from each lens surface is disposed at each of conjugate positions $P'_1$ and $P'_2$, thereby preventing the reflected light from mixing with the phototaking light beam. When, at the points $P_1$ and $P_2$ of the reflected image position, the reflected image of each surface is all in real conjugate relation, the same effect can of course be obtained even if a real black point is placed at the conjugate position of the objective lens.

Numerical data of the first embodiment as the first type shown in FIG. 4 and the second embodiment as the second type shown in FIG. 5 will be shown below. In the tables below, d0 represents the distance between the examined eye and the vertex of the first surface $r_1$ of the objective lens, namely, the operating distance, $d_{6'}$ in the first embodiment and $d_{7'}$ in the second embodiment respectively represent the distance between the last surface of the objective lens and the center of the opening portion of the apertured mirror.

FIRST EMBODIMENT

|  | d0 = 34.55 |  |  |
|---|---|---|---|
| r1 = −119.036 | $d_{1'}$ = 20.0 | n1 = 1.62041 | ν1 = 60.3 |
| r2* = −29.510* | $d_{2'}$ = 1.0 |  |  |
| r3 = 75.617 | $d_{3'}$ = 18.0 | n2 = 1.62041 | ν2 = 60.3 |
| r30 = −117.082 | $d_{4'}$ = 2.0 | n3 = 1.74000 | ν3 = 28.2 |
| r31 = 47.507 | $d_{5'}$ = 25.0 | n4 = 1.69350 | ν4 = 53.6 |
| r4 = −179.690 | $d_{6'}$ = 131.4 |  |  | the surface with mark * - nonspherical surface
(first surface)
$P_1$ - vertex position of the last surface r4
$P_2$ - 53.36 mm from the vertex of the last surface r4

SECOND EMBODIMENT

|  | d0 = 32.58 |  |  |
|---|---|---|---|
| r1* = −121.343* | $d'_1$ = 14.0 | n1 = 1.62041 | ν1 = 60.3 |
| r2 = −39.036 | $d'_2$ = 0.5 |  |  |
| r3 = 135.880 | $d'_3$ = 12.0 | n2 = 1.62041 | ν2 = 60.3 |
| r4 = −95.499 | $d'_4$ = 0.5 |  |  |
| r5* = 42.301* | $d'_5$ = 40.0 | n3 = 1.62041 | ν3 = 60.3 |
| r51 = −34.450 | $d'_6$ = 2.0 | n4 = 1.75520 | ν4 = 27.5 |
| r6 = 90.000 | $d'_7$ = 90.0 |  |  | the surface with mark *—nonspherical surface
(second surface)
$P_1$—8.72 mm from the vertex of the last surface r6
$P_2$—57.21 mm from the vertex of the last surface r6

Figure 6:
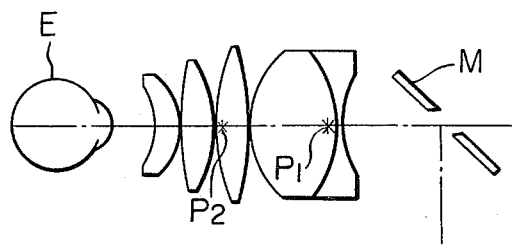
FIG. 6 shows an example in which a positive lens is further added to the objective lens of FIG. 5.

FIG. 6 shows an example in which a positive lens is added to the objective lens of the second type shown in FIG. 5 to provide a wider angle of view. Again in such a case, as described above, depending on whether the lens surface is adjacent to the examined eye side or the apertured mirror side, the reflected image is concentrated while being divided into two locations, i.e. the points $P_1$ and $P_2$, and a black point or a black point image is provided or formed at each of these two locations, whereby harmful reflected light in the lens surface can be sufficiently intercepted while a very wide angle of view is maintained. Again in the construction of the first type shown in FIG. 4, a wide angle of view can be provided by adding a positive lens while keeping said relation. In both types, a wider angle of view can be provided by increasing the number of positive lenses, but generally the operating distance becomes shorter and therefore, the number of lenses is naturally limited.

According to the construction of the present invention as described above, even if the number of lenses is increased, the reflected light in each lens surface can be sufficiently intercepted and an excellent observed image and photographed image can be obtained while keeping a very wide angle of view.

I claim:

1. An eye fundus observing and photographing optical system comprising an objective lens including a biconvex main positive lens component and at least one positive lens component provided at that side of said main positive lens component which is adjacent to an eye to be examined, and an illuminating optical system including an apertured mirror disposed obliquely with respect to the optical axis of said objective lens to supply an illuminating light to the fundus of said eye through said objective lens, the reflected image position of the opening portion of said apertured mirror by the eye-side lens surface of said at least one positive lens component being substantially coincident with a first position whereat the reflected image of the opening portion of said apertured mirror by the eye-side lens surface of said biconvex main positive lens component is formed, and the reflected image position of the opening portion of said apertured mirror by the apertured mirror-side lens surface of said at least one positive lens component being substantially coincident with a second position whereat the reflected image of the opening portion of said apertured mirror by the apertured mirror-side lens surface of said biconvex main positive lens component is formed, said second position being more adjacent to said eye than said first position;

said biconvex main positive lens component having in itself a first cemented surface having its convex surface facing said apertured mirror and a second cemented surface having its concave surface facing to said apertured mirror, said second cemented surface being disposed at the apertured mirror side of said first cemented surface, the reflected image position of the opening of said apertured mirror by said first cemented surface being substantially coincident with said second position, and the reflected image position of the opening portion of said apertured mirror by said second cemented surface being substantially coincident with said first position;

wherein when the distance from the vertex of the lens surface of said at least one positive lens component which is most adjacent to said eye to the vertex of the lens surface of said main positive lens component which is adjacent to said eye is d1 and the center thickness of said main positive lens component is d2 and when the vertex of the lens surface of said main positive lens component which is adjacent to said apertured mirror is the origin of the coordinates and the apertured mirror side is the positive direction, the distance $P_1$ to said first position and the distance $P_2$ to said second position satisfy the following conditions:

$$-\tfrac{1}{3}d_2 \leq P_1 < d_2 \tag{I}$$

$$-(2d_1 + d_2) \leq P_2 < d_1/4 - d_2; \text{ and} \tag{II}$$

wherein numerical data are as follows:

FIRST EMBODIMENT

| | $d_0 = 34.55$ | | |
|---|---|---|---|
| $r_1 = -119.036$ | $d_{1'} = 20.0$ | $n_1 = 1.62041$ | $\nu_1 = 60.3$ |
| $r_2* = -29.510*$ | $d_{2'} = 1.0$ | | |
| $r_3 = 75.617$ | $d_{3'} = 18.0$ | $n_2 = 1.62041$ | $\nu_2 = 60.3$ |
| $r_{30} = -117.082$ | $d_{4'} = 2.0$ | $n_3 = 1.74000$ | $\nu_3 = 28.2$ |
| $r_{31} = 47.507$ | $d_{5'} = 25.0$ | $n_4 = 1.69350$ | $\nu_4 = 53.6$ |
| $r_4 = -179.690$ | $d_{6'} = 131.4$ | | |

{ the surface with mark * - nonspherical surface (first surface)
$P_1$ - vertex position of the last surface $r_4$
$P_2$ - 53.36 mm from the vertex of the last surface $r_4$ } wherein r represents the curvature radius of each lens surface, d' represents the center thickness of and the air space between each lens, n represents the refractive index, $\nu$ represents Abbe number, and the added numerals represent the order from the eye to be examined, and wherein d0 represents the distance between the eye to be examined and the first lens surface ($r_1$), and $r_{30}$ and $r_{31}$ represent the curvature radii of the cemented surfaces in the biconvex main positive lens component.

2. An eye fundus observing and photographing optical system comprising an objective lens including a positive meniscus main lens component having its convex surface facing the eye-side and at least two positive lens components provided at that side of said main positive lens component which is adjacent to an eye to be examined, and an illuminating optical system including an apertured mirror disposed obliquely with respect to the optical axis of said objective lens to supply an illuminating light to the fundus of said eye through said objective lens, the center of curvature of the concave lens surface of said positive meniscus main positive lens component which is adjacent to said apertured mirror being substantially coincident with a position intersecting the optical axis of said apertured mirror, the reflected image positions of the opening portion of said apertured mirror by the eye-side lens surfaces of said respective two positive lens components being substantially coincident with a first position whereat the reflected image of the opening portion of said apertured mirror by the eye-side lens surface of said positive meniscus main lens component is formed, and the reflected image positions of the opening portion of said apertured mirror by the apertured mirror-side lens surfaces of said respective at least two positive lens components being substantially coincident with a second position which is more adjacent to said eye than said first position; said positive meniscus main lens component having in itself a cemented surface having its convex surface facing to said apertured mirror, the reflected image position of the opening of said apertured mirror by said cemented surface being substantially coincident with said first position; and wherein, when the distance from the vertex of the lens surface of said at least two positive lens component which is most adjacent to said eye to the vertex of the lens surface of said positive meniscus main lens component which is adjacent to said eye is $d_1$ and the center thickness of said positive meniscus main lens component is $d_2$ and when the vertex of the lens surface of said positive meniscus main positive lens component which is adjacent to said apertured mirror is the origin of the coordinates and the apertured mirror side is the positive direction, the distance $P_1$ to said first position and the distance $P_2$ to said second position satisfy the following condition:

$$-\tfrac{1}{2}d_2 \leq P_1 < d_2 \quad (I)$$

$$-(2d_1+d_2) \leq P_2 < (d_1/4)-d_2 \quad (II)$$

wherein numerical data are as follows:

SECOND EMBODIMENT

| | $d_0 = 32.58$ | | |
|---|---|---|---|
| $r_1* = -121.343*$ | $d'_1 = 14.0$ | $n_1 = 1.62041$ | $\nu_1 = 60.3$ |
| $r_2 = -39.036$ | $d'_2 = 0.5$ | | |
| $r_3 = 135.880$ | $d'_3 = 12.0$ | $n_2 = 1.62041$ | $\nu_2 = 60.3$ |
| $r_4 = -95.499$ | $d'_4 = 0.5$ | | |
| $r_5* = 42.301*$ | $d'_5 = 40.0$ | $n_3 = 1.62041$ | $\nu_3 = 60.3$ |
| $r_{51} = -34.450$ | $d'_6 = 2.0$ | $n_4 = 1.75520$ | $\nu_4 = 27.5$ |
| $r_6 = 90.000$ | $d'_7 = 90.0$ | | |

{ the surface with mark *—nonspherical surface (second surface)
$P_1$—8.72 mm from the vertex of the last surface $r_6$
$P_2$—57.21 mm from the vertex of the last surface $r_6$ } wherein r represents the curvature radius of each lens surface, d' represents the center thickness of and the air space between each lens, n represents the refractive index, $\nu$ represents Abbe number, and the added numerals represent the order from the eye to be examined, and wherein d0 represents the distance between the eye to be examined and the first lens surface ($r_1$), and $r_{51}$ represents the curvature radius of the cemented surface in the positive meniscus main lens component.

* * * * *

UNITED STATES PATENT AND TRADEMARK OFFICE
CERTIFICATE OF CORRECTION

PATENT NO. : 4,423,932
DATED : January 3, 1984
INVENTOR(S) : FUMIO TAKAHASHI

It is certified that error appears in the above-identified patent and that said Letters Patent is hereby corrected as shown below:

Column 5, line 50, "of" should be --or--.

*Signed and Sealed this*

*Twentieth* Day of *March 1984*

[SEAL]

*Attest:*

GERALD J. MOSSINGHOFF

*Attesting Officer* — *Commissioner of Patents and Trademarks*